(12) United States Patent
Kim et al.

(10) Patent No.: US 11,619,633 B2
(45) Date of Patent: Apr. 4, 2023

(54) DNA APTAMER SPECIFICALLY BINDING TO ESAT6, AND USE THEREOF

(71) Applicant: MD APTUS INC., Seoul (KR)

(72) Inventors: Yoon-Keun Kim, Gyeonggi-do (KR); Changill Ban, Gyeongsangbuk-do (KR); Chulhun Chang, Busan (KR)

(73) Assignee: MD APTUS INC., Seoul (KR)

( * ) Notice: Subject to any disclaimer, the term of this patent is extended or adjusted under 35 U.S.C. 154(b) by 445 days.

(21) Appl. No.: 16/649,747

(22) PCT Filed: Sep. 19, 2018

(86) PCT No.: PCT/KR2018/011066
§ 371 (c)(1),
(2) Date: Mar. 23, 2020

(87) PCT Pub. No.: WO2019/059644
PCT Pub. Date: Mar. 28, 2019

(65) Prior Publication Data
US 2020/0340992 A1    Oct. 29, 2020

(30) Foreign Application Priority Data

Sep. 25, 2017  (KR) .................. 10-2017-0123384

(51) Int. Cl.
| | | |
|---|---|---|
| *C07H 21/02* | (2006.01) | |
| *G01N 33/569* | (2006.01) | |
| *C12N 15/115* | (2010.01) | |
| *G01N 33/553* | (2006.01) | |

(52) U.S. Cl.
CPC ....... *G01N 33/5695* (2013.01); *C12N 15/115* (2013.01); *G01N 33/553* (2013.01); *C12N 2310/16* (2013.01); *G01N 2800/26* (2013.01)

(58) Field of Classification Search
None
See application file for complete search history.

(56) References Cited

FOREIGN PATENT DOCUMENTS

| JP | 6190355 B2 | 8/2017 |
| KR | 20160077788 A | 7/2016 |
| WO | 2011014989 A1 | 2/2011 |

OTHER PUBLICATIONS

Ma, Z.-Z. "Screening and affinity analysis of aptamers to ESAT-6 protein from *Mycobacterium tuberculosis*", Chinese Journal of Clinicians, 2007, vol. 5.
Tang, X.-L. et al., "CFP10 and ESAT6 aptamers as effective Mycobacterial antigen diagnostic reagents", The Journal of Infection, 2014, vol. 69, pp. 569-580.
Rotherham, L. S. et al., "Selection and application of ssDNA aptamers to detect active TB from sputum samples", PLOS One, Oct. 2012., vol. 7(10), e46862, pp. 1-11.

*Primary Examiner* — Jennifer E Graser
(74) *Attorney, Agent, or Firm* — Riverside Law LLP (57) ABSTRACT

The present invention relates to a DNA aptamer binding specifically to early secretory antigenic target 6 kDa (ESAT6), a biosensor for diagnosis of tuberculosis, comprising the same, and a method for providing information for diagnosis of tuberculosis. The present inventors found that not only does a DNA aptamer according to the present invention have specific binding potential to ESAT6 protein, but also the binding affinity is excellent. When used, the DNA aptamer of the present invention can be thus expected to exhibit greater stability than a conventional ELISA method using an antibody. Hence, the aptamer is expected to find useful applications in the development of compositions for tuberculosis diagnosis, biosensors for tuberculosis diagnosis, and information providing methods for tuberculosis diagnosis.

9 Claims, 9 Drawing Sheets

Specification includes a Sequence Listing.

SEQUENCE LISTING

```
<160> NUMBER OF SEQ ID NOS: 6

<210> SEQ ID NO 1
<211> LENGTH: 32
<212> TYPE: DNA
<213> ORGANISM: Artificial Sequence
<220> FEATURE:
<223> OTHER INFORMATION: ESAT6 Forward primer

<400> SEQUENCE: 1
cccggatcca tgacagagca gcagtggaat tt                                32

<210> SEQ ID NO 2
<211> LENGTH: 31
<212> TYPE: DNA
<213> ORGANISM: Artificial Sequence
<220> FEATURE:
<223> OTHER INFORMATION: ESAT6 Reverse primer

<400> SEQUENCE: 2
cccccaagct tctatgcgaa catcccagtg a                                 31

<210> SEQ ID NO 3
<211> LENGTH: 51
<212> TYPE: DNA
<213> ORGANISM: Artificial Sequence
<220> FEATURE:
<223> OTHER INFORMATION: ssDNA library
<220> FEATURE:
<221> NAME/KEY: misc_feature
<222> LOCATION: (32)..(32)
<223> OTHER INFORMATION: n is a, c, g, or t

<400> SEQUENCE: 3
cacctaatac gactcactat agcggatccg anctggctcg aacaagcttg c           51

<210> SEQ ID NO 4
<211> LENGTH: 26
<212> TYPE: DNA
<213> ORGANISM: Artificial Sequence
<220> FEATURE:
<223> OTHER INFORMATION: Forward primer

<400> SEQUENCE: 4
cacctaatac gactcactat agcgga                                      26

<210> SEQ ID NO 5
<211> LENGTH: 19
<212> TYPE: DNA
<213> ORGANISM: Artificial Sequence
<220> FEATURE:
<223> OTHER INFORMATION: Reverse primer

<400> SEQUENCE: 5
gcaagcttgt tcgagccag                                              19
```

```
<210> SEQ ID NO 6
<211> LENGTH: 44
<212> TYPE: DNA
<213> ORGANISM: Artificial Sequence
<220> FEATURE:
<223> OTHER INFORMATION: EG11(44) Aptamer

<400> SEQUENCE: 6
cgaggtagct tacccgctta tgttcactgt gggttgctgg ctcg                    44
```

DNA APTAMER SPECIFICALLY BINDING TO ESAT6, AND USE THEREOF

CROSS-REFERENCE TO RELATED APPLICATIONS

This application is the U.S. national phase application filed under 35 U.S.C. § 371 claiming benefit to International Patent Application No. PCT/KR2018/011066, filed on Sep. 19, 2018, which claims priority to Korean Patent Application No. 10-2017-0123384, filed Sep. 25, 2017, the disclosures of which are incorporated herein by reference in their entirety.

TECHNICAL FIELD

The present invention relates to an aptamer for protein detection, and more particularly to a DNA aptamer that specifically binds to early secretory antigenic target 6 kDa (ESAT6), which is known to be expressed in *Mycobacterium Tuberculosis* H37Rv.

BACKGROUND ART

Tuberculosis is a common and fatal disease that results from infection with *Mycobacterium tuberculosis*. Symptoms of tuberculosis include sudden weight loss due to anorexia, high fever, and coughing accompanied by bloody phlegm. Diagnostic methods include X-ray inspection, a sputum smear test, and polymerase chain reaction (PCR), and tuberculosis is finally diagnosed by a combination thereof.

Tuberculosis is commonly known to occur frequently in developing countries, including the African region, and has recently been recognized as an eradicated disease. However, according to the World Health Organization's statistics, it is a terrible disease that ranks among the top 10 causes of death worldwide in 2015, and particularly, Korea disgracefully ranks first by overwhelming numbers in terms of tuberculosis incidence and mortality among OECD countries. Thus, Korea established national guidelines for tuberculosis management, the biggest problem is the diagnosis of latent tuberculosis, and the number of latent tuberculosis patients is estimated to be 2 billion people, which corresponds to one third of the world's population. 10% of latent tuberculosis progresses to active tuberculosis, and it is important to perform early diagnosis and treatment before the onset of symptoms thereof.

Currently, the diagnosis of latent tuberculosis is based on two tests: tuberculin skin test (TST) and interferon-gamma releasing assay (IGRA). The TST takes a minimum of 48 hours to 72 hours and may show false-positive results by BCG vaccination or infection with non-tuberculous mycobacteria. The IGRA is an indirect diagnosis method in which blood of a patient is added to a tube with a *Mycobacterium tuberculosis*-specific antigen attached thereto, followed by stimulation for 16 hours and then measuring the secretion of interferon-gamma. Compared to TST, the rate of false-positive results is low due to the use of a *Mycobacterium tuberculosis*-specific antigen, but the lack of stability is a drawback when considering that the epidemic area of tuberculosis is mostly hot or humid. In addition, the secretion of IFN-g is indirectly measured through stimulation in the blood, and thus there is a drawback such as reduced sensitivity.

Meanwhile, ESAT6 is known to be overexpressed in *Mycobacterium tuberculosis* H37Rv, which causes deadly tuberculosis in humans. The mechanism of disease induction in a host during infection is not known accurately, but it is assumed through IGRA that ESAT6 forms a complex with CFP-10 or TB7.7, which is used as a *Mycobacterium tuberculosis*-specific antigen for IFN-g secretion to mediate a Th1 cellular immune response.

An aptamer is a single-stranded DNA (ssDNA) or RNA having high specificity and affinity for a specific substance, and has recently been actively developed due to very high and stable affinity for a specific substance and application thereof to therapeutic agents and diagnostic sensors is actively ongoing (see Korean Patent Registration No. 10-1279585). An aptamer can be synthesized using a relatively simple method and can target a cell, a protein, and even a small organic substance, and thus it is possible to develop novel detection methods using the same, and since the specificity and stability thereof are much higher than previously developed antibodies, application thereof to the development of therapeutic agents, drug delivery systems, and diagnostic biosensors is possible, and therefore, research thereon continues to be conducted.

DESCRIPTION OF EMBODIMENTS

Technical Problem

As a result of having made intensive efforts to develop an aptamer capable of replacing an antibody against early secretory antigenic target 6 kDa (ESAT6), the inventors of the present invention produced a DNA aptamer having a specific binding capacity for the ESAT6 protein, and thus completed the present invention based on this finding.

Therefore, an object of the present invention is to provide a DNA aptamer that specifically binds to early secretory antigenic target 6 kDa (ESAT6), wherein the DNA aptamer consists of a nucleotide sequence of SEQ ID NO: 6.

Another object of the present invention is to provide a composition for diagnosing tuberculosis including the DNA aptamer.

Still another object of the present invention is to provide a biosensor for diagnosing tuberculosis including a DNA aptamer specific to early secretory antigenic target 6 kDa (ESAT6); and a board on which the DNA aptamer is immobilized, wherein the DNA aptamer consists of a nucleotide sequence of SEQ ID NO: 6.

Yet another object of the present invention is to provide a method of providing information for diagnosing tuberculosis, including: (1) treating a subject sample to the biosensor; and (2) measuring a level of early secretory antigenic target 6 kDa (ESAT6) bound to the biosensor.

However, technical problems to be solved by the present invention are not limited to the above-described technical problems, and other unmentioned technical problems will become apparent from the following description to those of ordinary skill in the art.

Technical Solution

According to an aspect of the present invention, there is provided a DNA aptamer that specifically binds to early secretory antigenic target 6 kDa (ESAT6), wherein the DNA aptamer consists of a nucleotide sequence of SEQ ID NO: 6.

In one embodiment of the present invention, the ESAT6 may be expressed in *Mycobacterium tuberculosis* H37Rv, but the present invention is not limited thereto.

The present invention also provides a composition for diagnosing tuberculosis including the DNA aptamer.

The present invention also provides a biosensor for diagnosing tuberculosis including: a DNA aptamer specific to early secretory antigenic target 6 kDa (ESAT6); and a board on which the DNA aptamer is immobilized, wherein the DNA aptamer consists of a nucleotide sequence of SEQ ID NO: 6.

In one embodiment of the present invention, the board may consist of a metal electrode layer and a metal nanoparticle layer, and the metal may be, preferably, gold (Au), but the present invention is not limited thereto.

The present invention also provides a method of providing information for diagnosing tuberculosis, including: (1) treating a subject sample to the biosensor; and (2) measuring a level of early secretory antigenic target 6 kDa (ESAT6) bound to the biosensor.

The present invention also provides a method of diagnosing tuberculosis, including bringing the DNA aptamer into contact with a subject sample.

The present invention also provides a method of diagnosing tuberculosis, including: treating a subject sample to the biosensor; and measuring a level of ESAT6 bound to the biosensor.

In one embodiment of the present invention, the subject sample may be blood of an individual in need of diagnosis of tuberculosis, and the blood may be whole blood, serum, plasma, or blood monocytes.

The present invention also provides a use of a DNA aptamer for diagnosing tuberculosis, the DNA aptamer specifically binding to early secretory antigenic target 6 kDa (ESAT6).

Advantageous Effects of Invention

A DNA aptamer according to the present invention has a specific binding capacity for the early secretory antigenic target 6 kDa (ESAT6) protein, and the binding ability thereof is excellent, and thus false-negative responses can be excluded in the diagnosis of tuberculosis. In addition, the DNA aptamer of the present invention has a high affinity with a target (ESAT6) and high exclusivity for substances other than the target so that false-positive responses can be excluded in the diagnosis of tuberculosis. Thus, when the DNA aptamer of the present invention is used, excellent stability can be expected compared to an ELISA method using existing antibodies, and thus the aptamer is expected to be usefully applied to the development of a composition for diagnosing tuberculosis, a biosensor for diagnosing tuberculosis, a method of providing information for diagnosing tuberculosis, and the like.

BEST MODE

As a result of having made intensive efforts to develop an aptamer capable of replacing an antibody against early secretory antigenic target 6 kDa (ESAT6), the inventors of the present invention expressed ESAT6 in a bacteria expression system and purified the expressed ESAT6 and selected aptamers using a systematic evolution of ligands by exponential enrichment (SELEX) technique, established the sequences and structures of DNA aptamers, and confirmed the ability of the DNA aptamers produced in the present invention to specifically bind to the early secretory antigenic target 6 kDa (ESAT6) protein, and thus completed the present invention based on this finding.

Hereinafter, the present invention will be described in detail.

The present invention provides a DNA aptamer that specifically binds to early secretory antigenic target 6 kDa (ESAT6), wherein the DNA aptamer consists of a nucleotide sequence of SEQ ID NO: 6.

In the present invention, "early secretory antigenic target 6 kDa (ESAT6)" is a 6 kDa early secretory antigenic target produced by *Mycobacterium tuberculosis*, a secretory protein, and a potent T cell antigen. The ESAT6 is used in tuberculosis diagnosis by QuantiFERON-TB Gold, which is a whole blood interferon γ test, together with CFP10 and TB7.7, and is also known to directly bind to the TLR2 receptor and inhibit downstream signal transduction.

As used herein, the term "aptamer" refers to single-stranded DNA (ssDNA) or RNA having high specificity and affinity for a specific substance. Methods using previously developed antibodies use an immune system of the living body, and thus take a relatively large amount of time and cost, and the stability thereof is sometimes problematic because these antibodies are proteins, whereas an aptamer can be synthesized using a relatively simple method and target a cell, a protein, and even a small organic substance, and thus enables the development of new detection methods using the aptamer, and based on very high specificity and stability thereof compared to previously developed antibodies, a DNA aptamer was used for specific detection of the ESAT6 protein. The aptamer may consist of, preferably, a nucleotide sequence of SEQ ID NO: 6, but the present invention is not limited thereto.

The present invention also provides a composition for diagnosing tuberculosis, including the DNA aptamer.

The composition of the present invention may further include a pharmacologically or physiologically acceptable carrier, excipient, and diluent in addition to the DNA aptamer, and examples of carriers, excipients, and diluents that may be included in the composition include lactose, dextrose, sucrose, sorbitol, mannitol, xylitol, erythritol, maltitol, starch, acacia gum, alginates, gelatin, calcium phosphate, calcium silicate, cellulose, methyl cellulose, amorphous cellulose, polyvinylpyrrolidone, water, methylhydroxy benzoate, propylhydroxy benzoate, talc, magnesium stearate, mineral oil, and the like. When formulated, the composition may further include a filler, a thickener, a binder, a disintegrating agent, a surfactant, an anti-coagulant, a lubricant, a wetting agent, a fragrance, an emulsifying agent, a preservative, and the like, which are commonly used.

The present invention also provides a biosensor for diagnosing tuberculosis, including: a DNA aptamer specific to early secretory antigenic target 6 kDa (ESAT6); and a board on which the DNA aptamer is immobilized, wherein the DNA aptamer consists of a nucleotide sequence of SEQ ID NO: 6.

The board on which the DNA aptamer of the present invention is immobilized may consist of a metal electrode layer and a metal nanoparticle layer, and the material of the electrode layer and nanoparticles may be attracted by an electric or magnetic field and may be any material capable of changing the characteristics of an electric field, preferably gold (Au), but the present invention is not limited thereto.

In one embodiment of the present invention, a specific binding sequence was identified by expressing and purifying the early secretory antigenic target 6 kDa (ESAT6) protein (see Examples 1 to 3), and an aptamer having strong binding ability with the ESAT6 protein was screened (see Example 4). In addition, based on the above experimental results, the binding force between the protein and the aptamer was measured by fluorescence, and it was measured by an EMSA method whether the aptamer actually binds to the ESAT6 protein (see Examples 5 and 6), and through the results thereof, a biosensor for detecting ESAT6 was manufactured using an EIS method using the found DNA aptamer (see Example 7). It was also confirmed that the biosensor also has very high binding specificity for the ESAT6 protein, and thus could be used as a method of providing information for diagnosing tuberculosis (see Example 8).

Therefore, the present invention provides a method of providing information for diagnosing tuberculosis, including: (1) treating a subject sample to the biosensor; and (2) measuring a level of early secretory antigenic target 6 kDa (ESAT6) bound to the biosensor.

In the present invention, a subject is not limited as long as the subject is an individual in need of diagnosis of tuberculosis, and the individual includes mammals and non-mammals, and the mammals include mice, livestock, humans, and the like, but preferably humans.

In addition, in the present invention, the subject sample may be blood of an individual in need of diagnosis of tuberculosis, and the blood may be whole blood, serum, plasma, or blood monocytes.

MODE OF INVENTION

Hereinafter, exemplary examples will be described to aid in understanding of the present invention. However, the following examples are provided to facilitate the understanding of the present invention and are not intended to limit the scope of the present invention.

Example 1

ESAT6 Gene Cloning

To amplify the gene for early secretory antigenic target 6 kDa (ESAT6), a forward primer including a BamH1 restriction enzyme recognition sequence (5'-CCC GGATCC ATG ACA GAG CAG CAG TGG AAT TT3' (SEQ ID NO: 1)) and a reverse primer including a Hind3 restriction enzyme recognition sequence (5'CCC CCA AGC TTC TAT GCG AAC ATC CCA GTG A3' (SEQ ID NO: 2)) were used.

Genomic DNA of *Mycobacterium tuberculosis* H37Rv was used as a template for gene amplification and amplified by polymerase chain reaction (PCR) using i-pfu polymerase. Each process of the PCR is as follows: 1) incubation at 98☐ for 20 seconds as a process of denaturing double-stranded DNA as a template; 2) incubation at 57☐ for 20 seconds as a process of annealing the template with the primers; and 3) incubation at 72☐ for 30 seconds as a process of extending new strands, and a cycle of these processes was repeated 30 times.

The amplified ESAT6 gene was cloned into a pET32a vector containing (His) 6-tag through reaction with a restriction enzyme and a DNA ligase, and BL21 (DE3) *E. coli* cells were transformed with the vector.

Example 2

Expression of ESAT6 Protein

BL21(DE3) cells transformed with the ESAT6 gene were cultured in a Luria Bertani (LB) medium and cultured at 37☐ until optical density (OD) reached 0.563 at UV 600 nm. Thereafter, isopropyl-thio-b-D-galactopyranoside (IPTG) was added to a final concentration of 20 mM to induce expression of the protein, followed by incubation at 37☐ for 4 hours. The expression of the protein was confirmed by SDS PAGE, and the cells were separated from the medium using a centrifuge and washed once with PBS (10 mM sodium phosphate, 150 mM NaCl, pH 8.0) buffer.

Example 3

Purification of ESAT6 Protein

To purify the ESAT6 protein expressed in the bacterial cell BL21(DE3) with high purity, the cells were lysed in a cell lysis buffer (20 mM Tris, 500 mM NaCl, 0.5 mM β-mercaptoethanol, 5% glycerol, pH 8.0), and then ruptured by sonication using a sonicator for 15 minutes. Separation was carried out at 18,000 rpm for 40 minutes using a centrifuge to separate the protein in an aqueous solution state from the cells.

After centrifugation, the precipitate was added to and allowed to be resolved in a refolding buffer containing 8 M urea (8 M urea, 20 mM Tris-HCl, 500 mM NaCl, 15 mM imidazole, 0.5 mM β-mercaptoethanol, 5% glycerol, pH 8.0). Separation was carried out at 18,000 rpm for 50 minutes using a centrifuge to separate the protein resolved in an aqueous solution state from the cells.

Figure 1:
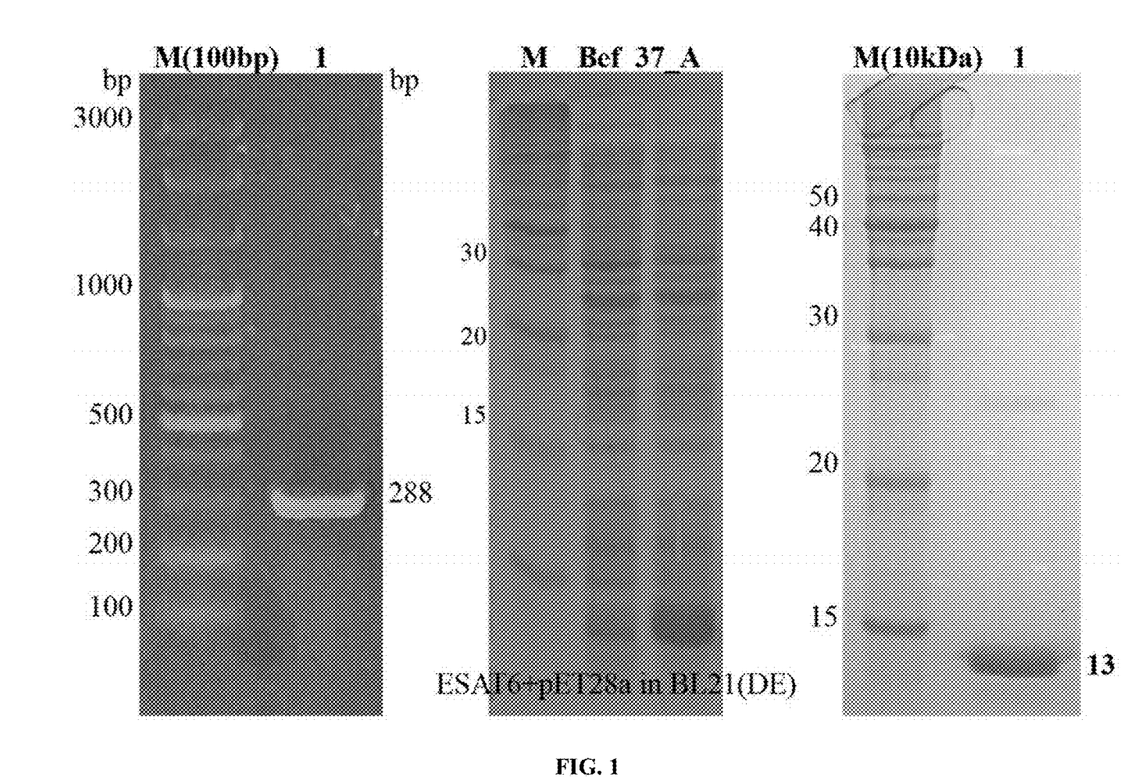
FIG. 1 illustrates the results of confirming overexpression of a recombinant ESAT6 protein by amplification of the ESAT6 gene (Bef lane denotes before inducing overexpression, and 37_A lane denotes overexpression induction results obtained by treatment with IPTG), and the results of observing a high-purity recombinant ESAT6 protein obtained through FPLC.
Figure 2:
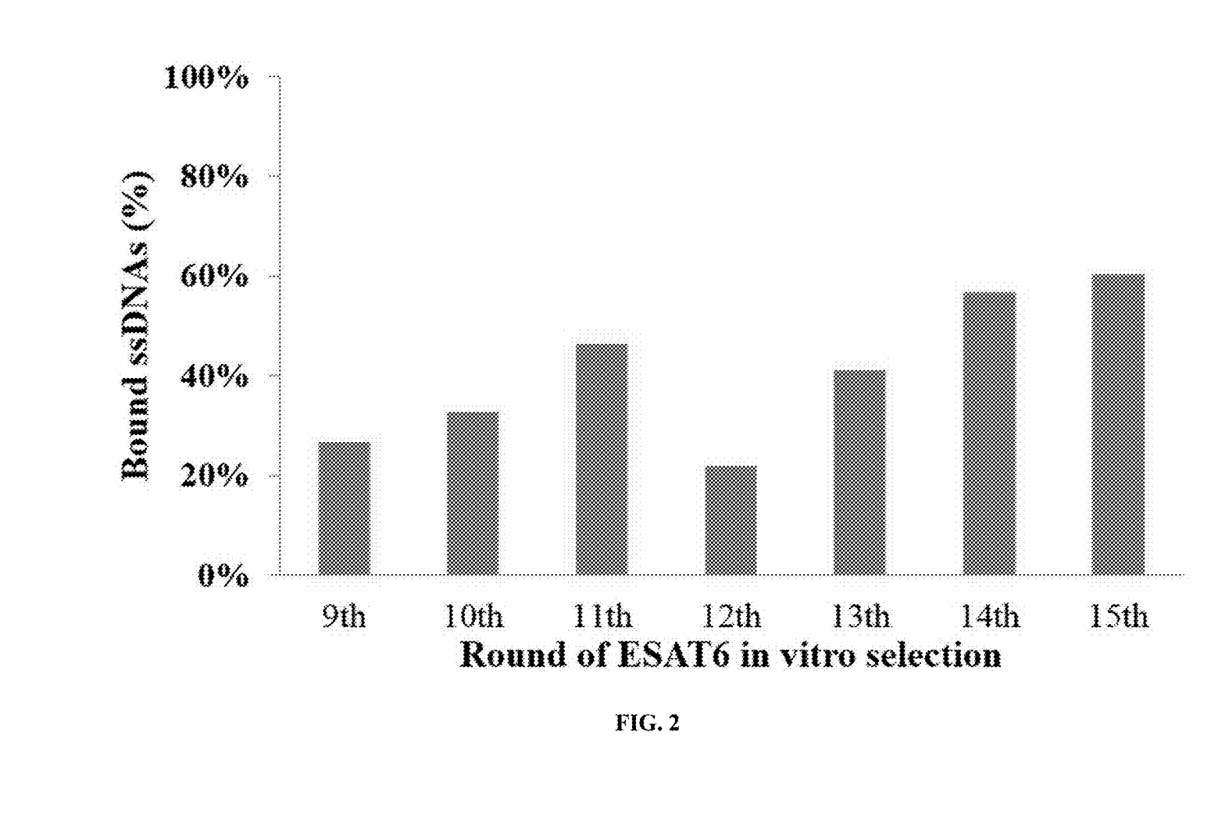
FIG. 2 illustrates the results of confirming the degree (%) of binding between single-stranded DNA (ssDNA) and ESAT6 and selection process results.
Figure 3:
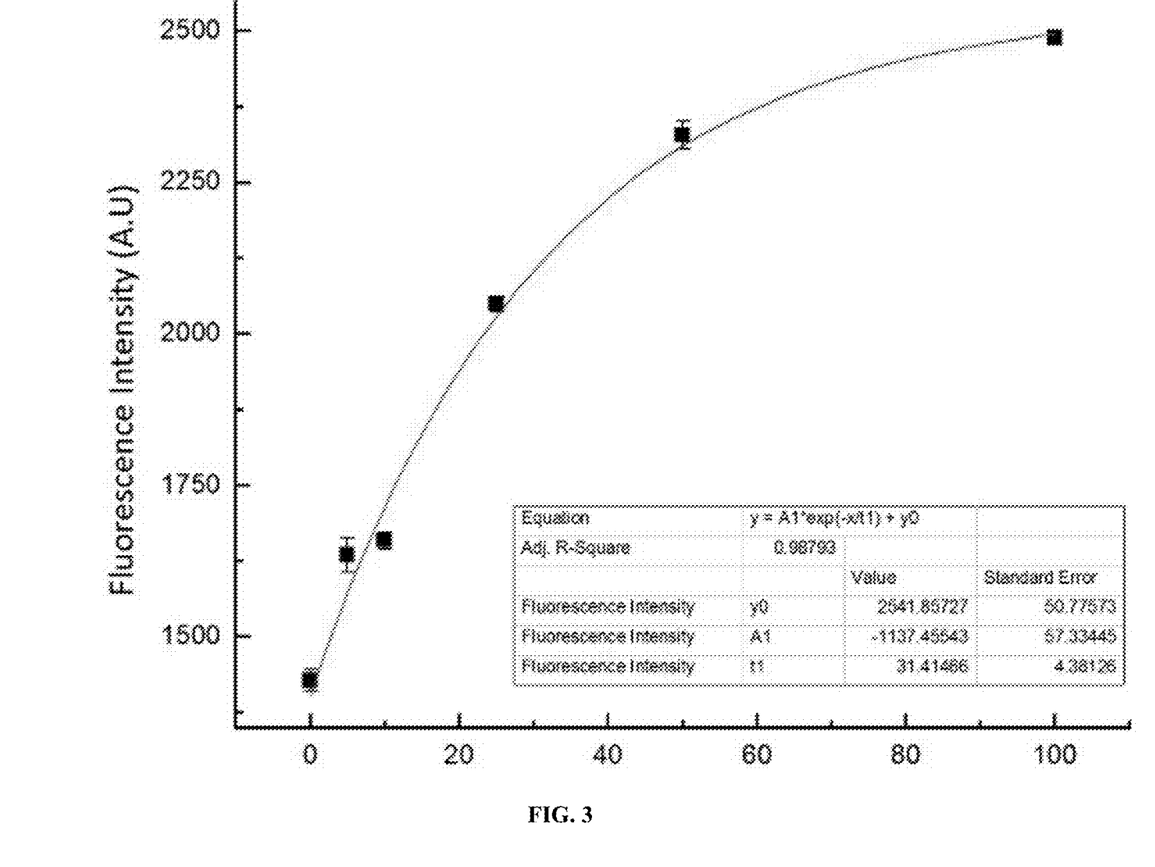
FIG. 3 illustrates the results of confirming a Kd value for an aptamer sequence through fluorescence measurement.

In addition, to obtain a high-purity protein, the property of binding between Ni-Nitrilotriacetic acid (Ni-NTA) and a (His)6-tag amino acid was used. Specifically, as illustrated in FIG. 1, a Ni-NTA column was connected to a fast protein liquid chromatography (FPLC) system, and ESAT6 in an aqueous solution state was flowed into the column, thus allowing the ESAT6 to bind thereto. Since the (His)6-tag of the protein bound to the Ni-NTA column competitively binds to an imidazole compound, to separate the target protein from the column, an elution buffer (20 mM Tris, 500 mM NaCl, 0.5 mM β-mercaptoethanol, 5% glycerol, 300 mM imidazole, pH 8.0) was sequentially flowed into the column, thereby isolating ESAT6 with high purity. Further, additional purification was performed to obtain a protein with higher purity from the isolated protein, and a MonoQ column, which is an ion exchange column that performs separation according to the pI value of a protein, was connected to the FPLC system, and then the aqueous protein solution was flowed thereinto. After binding to the column, ESAT6 was separated once again while sequentially flowing an elution buffer (50 mM Tris-HCl, 1 M NaCl, 0.5 mM β-mercaptoethanol, 5% glycerol, pH 8.00), thereby increasing purity. As a result, as illustrated in FIG. 1, a high-purity recombinant ESAT6 protein could be observed.

Example 4

Figure 4:
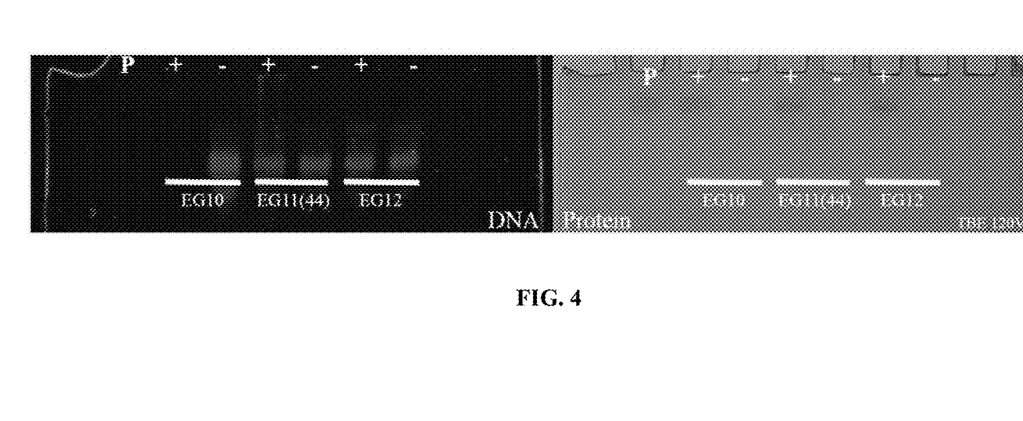
FIG. 4 illustrates the results of confirming whether EG10, EG11(44), and EG12 aptamers bind to the ESAT6 protein, through an electrophoric mobility shift assay (EMSA) method.

Screening of Aptamer for ESAT6 Protein Using SELEX 4-1. Preparation of Single-Stranded DNA (ssDNA) Library A synthetic library (5'-CACCTAATACGACTCAC-TATAGCGGATCCGA-N40-CTGGCTCGAACAAGCTTGC-3' (SEQ ID NO: 3)) having binding sequences of primers for PCR amplification and cloning at both ends thereof and having 90 sequences containing 40 random DNA bases in the middle) was designed. In addition, for PCR amplification and ssDNA production, a forward primer (5'-CAC CTA ATA CGA CTC ACT ATA GCG GA-3' (SEQ ID NO: 4)), a reverse primer (5'-GCA AGC TTG TTC GAG CCA G-3' (SEQ ID NO: 5)), and a biotin-coupled reverse primer (5'-Biotin-GCA AGC TTG TTC GAG CCA G-3') were used. All oligonucleotides used here were synthesized and PAGE-purified by Bionics (Korea).

4-2. Immobilization of ESAT6 on Ni-NTA Magnetic Beads

The purified ESAT6 was immobilized on beads using Dynalbeads (Invitrogen, Norway), which are magnetic beads which surfaces of which were coated with cobalt and which bind to His-tag of the protein.

Specifically, 1,500 pmole of protein dissolved in 100 μL of a protein binding buffer (20 mM Tris, 50 mM NaCl, 5 mM KCl, 5 mM $MgCl_2$, 0.01% Tween 20, pH 8.0) and 20 μl of beads were washed with a binding buffer using an external magnet, and then a reaction was allowed to occur therebetween at room temperature for 1 hour, thereby immobilizing the protein on the beads.

4-3. Selection of Aptamer Specific to ESAT6

A specific separation method using magnetism was carried out to select an aptamer specific to ESAT6.

Specifically, first, to form the most stable structure of ssDNA, a ssDNA library (100 pmole) dissolved in 100 μL of a binding buffer was incubated at 90□ for 3 minutes, and then pre-incubated at 4□ for 30 minutes. Subsequently, while the ssDNA library was gently shaken with the ESAT6 protein immobilized on the magnetic beads, a reaction was allowed to occur therebetween for 1 hour. Then, the beads were washed twice with a binding buffer to remove ssDNA that did not bind to the ESAT6 protein bound to the beads.

Thereafter, to separate the protein-bound ssDNA from the magnetic beads, the protein and the protein-bound ssDNA were eluted with an elution buffer (20 mM Tris, 50 mM NaCl, 5 mM KCl, 5 mM $MgCl_2$, 0.01% Tween 20, 300 mM imidazole, pH 8.0). The eluted ssDNA was precipitated using ethanol, and then dissolved in 60 μL of distilled water, followed by amplification using a forward primer and a biotin-coupled reverse primer by PCR using i-pfu polymerase (Intron Biotechnology, Korea). To produce ssDNA for the subsequent selection process, the biotin-coupled PCR product was incubated along with magnetic beads coated with streptavidin that binds to biotin, in the presence of a coupling buffer (5 mM Tris-HCl, 0.5 mM EDTA, 1 M NaCl, 0.0025% Tween 20, pH 7.5) for 1 hour. After incubation, to separate only ssDNA, the resulting product was incubated with 100 μl of 200 mM NaOH for 5 minutes, and only ssDNA selected using an external magnet was obtained. In addition, selection was repeated using the first selected ssDNA in the next selection. At this time, the amount of ssDNA and the concentration of ESAT6 were further reduced for strict selection, and the concentration of ssDNA eluted in the repeated selection was measured using a UV spectrometer (Biochrom Libra S22 spectrometer) to confirm the degree of binding between residual ssDNA and ESAT6, and the selection process was carried out. The degree (%) of binding is shown in FIG. 2.

4-4. Aptamer Sequencing

The $15^{th}$ repeatedly selected ssDNA was amplified by PCR using an unmodified forward primer and reverse primer, and cloned into a pENTR/TOPO vector (TOPO TA Cloning kit, Invitrogen, U.S.A.), and then *E. coli* TOP10 cells (Invitrogen, U.S.A.) were transformed with the vector. The clone into which ssDNA was inserted was purified using a Miniprep kit (MACHEREY-NAGEL, Germany), followed by sequencing (COSMO Genetech, Korea). As a result, the EG11(44) aptamer sequence (SEQ ID NO: 6) as shown in Table 1 below was analyzed.

TABLE 1

| Aptamer | Sequences (5' to 3') | Length (bases) |
|---|---|---|
| EG11(44) | 5'CGA GGT AGC TTA CCC GCT TAT GTT CAC TGT GGG TTG CTG GCT CG3' | 44 |

Example 5

Measurement of Bindin2 Force Between Protein and Aptamer Using Fluorescence Measurement 400 pmole of ESAT6 was mixed with 10 μL of magnetic beads, and then incubated in 100 μL of a binding buffer (20 mM Tris, 50 mM NaCl, 5 mM KCl, 5 mM $MgCl_2$, pH 8.0) for 1 hour. To separate unbound ESAT6, washing was performed twice with a binding buffer. Subsequently, the resulting mixture was incubated together with various concentrations of a Cy3-labeled aptamer, and an unbound aptamer was removed by washing. The amount of Cy3-labeled ssDNA aptamer bound to the magnetic beads with ESAT6 immobilized thereon was measured by fluorescence measurement (1420 Victor Multilabel counter, PerkinElmer, USA) by separating only Cy3-labeled ssDNA bound to ESAT6. As a result, as shown in FIG. 3 and Table 2 below, the Kd value of the DNA aptamer having a EG11(44) base sequence was measured.

TABLE 2

| Aptamer | Kd (nM) |
|---|---|
| EG11(44) | 31.4 ± 4.3 |

Example 6

Measurement of Bindin2 to ESAT6 Protein Using EMSA

To measure whether the EG11(44) aptamer selected through the systematic evolution of ligands by exponential enrichment (SELEX) technique of Example 4 actually binds to the ESAT6 protein, the inventors of the present invention confirmed the presence or absence of binding through an electrophoric mobility shift assay (EMSA) method. 5 µM of a recombinant ESAT6 protein and 1 µM of EG11(44), EG10, and EG12 aptamers were incubated in 20 µL of a binding buffer at room temperature for 1 hour, and then run on 6% acrylamide gel. As a result of SYBR green and Coomassie blue staining, as illustrated in FIG. 4, it was confirmed that the developed EG11(44) aptamer bound to ESAT6 better than the EG10 and EG12 aptamers.

Example 7

Optimization of Detection Conditions and Manufacture of Biosensor

Figure 5:
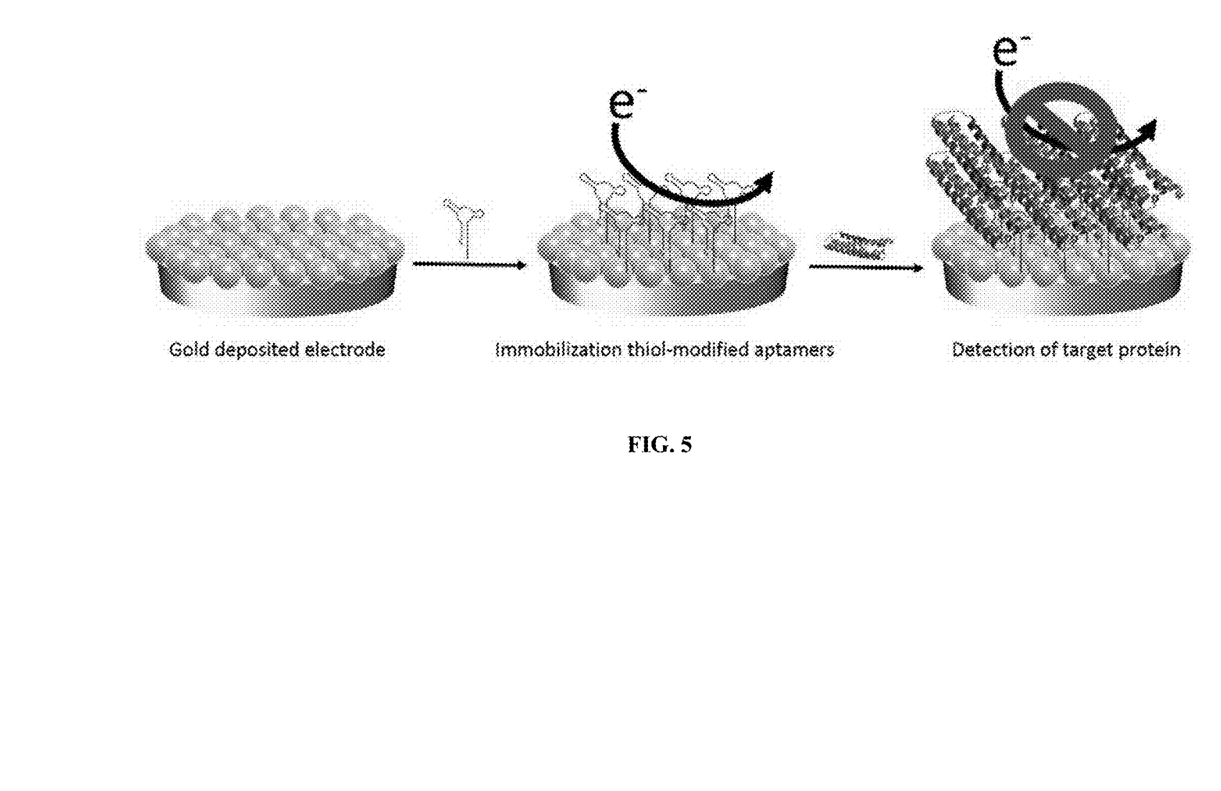
FIG. 5 is a schematic view of a biosensor for detecting the ESAT6 protein using the DNA aptamer.

To detect ESAT6 using the DNA aptamer discovered in Example 4, a biosensor having excellent detection sensitivity was designed using electrochemical impedance spectroscopy (EIS) technology. FIG. 5 is a schematic view of a biosensor for detecting the ESAT6 protein using the DNA aptamer of the present invention.

First, gold nanoparticles were adsorbed onto a gold electrode, and then the DNA aptamer was bound to the electrode, thereby completing the manufacture of a biosensor for detecting ESAT6. As such, when the gold electrode was coated with gold nanoparticles, the surface area thereof increased, and thus a greater number of DNA aptamers could bind to the electrode. Subsequently, when an ESAT6-containing sample was added and the aptamer and ESAT6 were bound to each other, the ESAT6 protein blocked the flow of electrons, and thus a phenomenon in which impedance increased was observed, and at this time, quantitative analysis was possible due to the correlation between the impedance increase and amount of the bound ESAT6 protein.

Figure 6A:
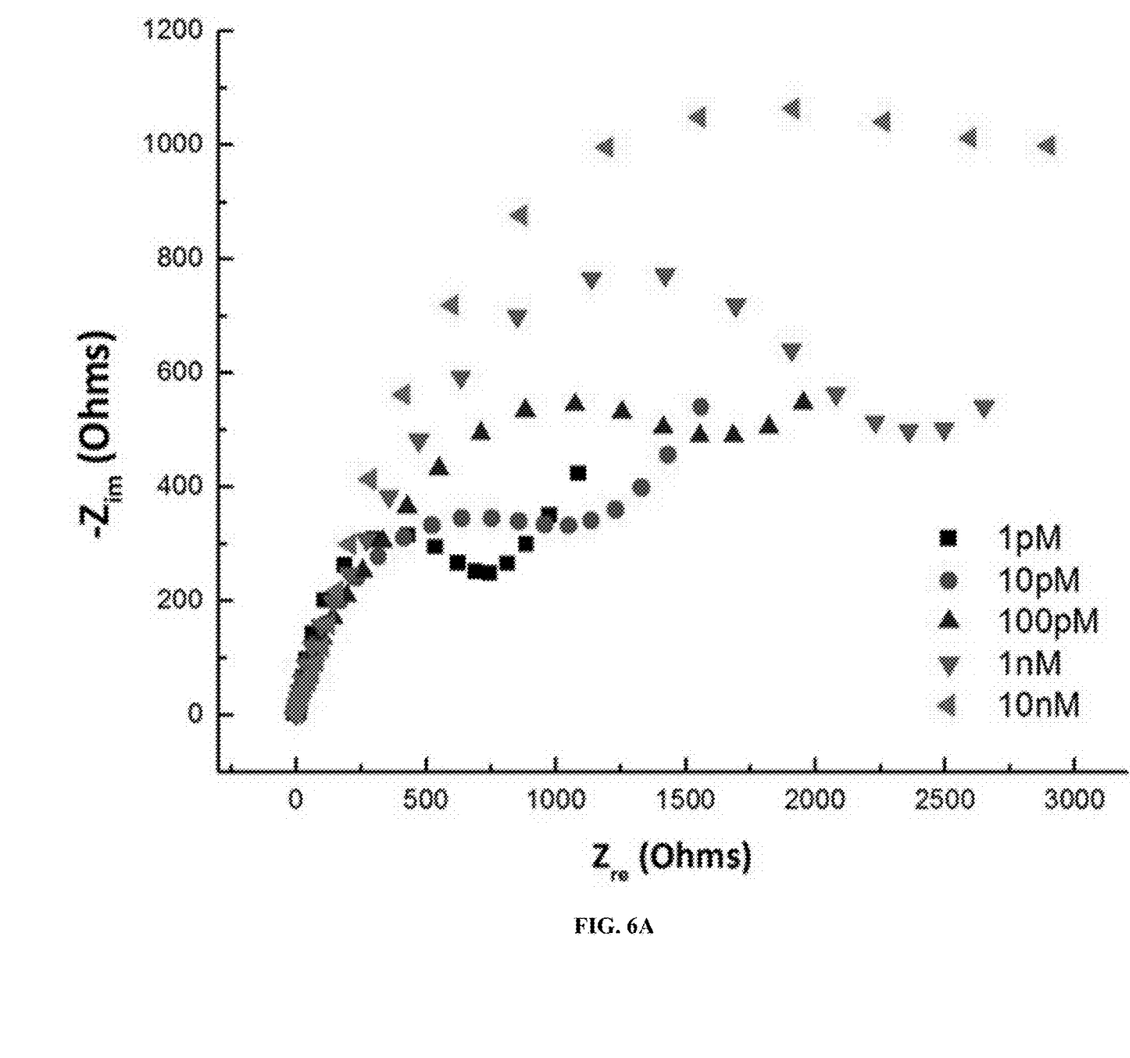
FIGS. 6A and 6B illustrate ESAT6 detection results obtained using an EG11(44) aptamer.
Figure 6B:
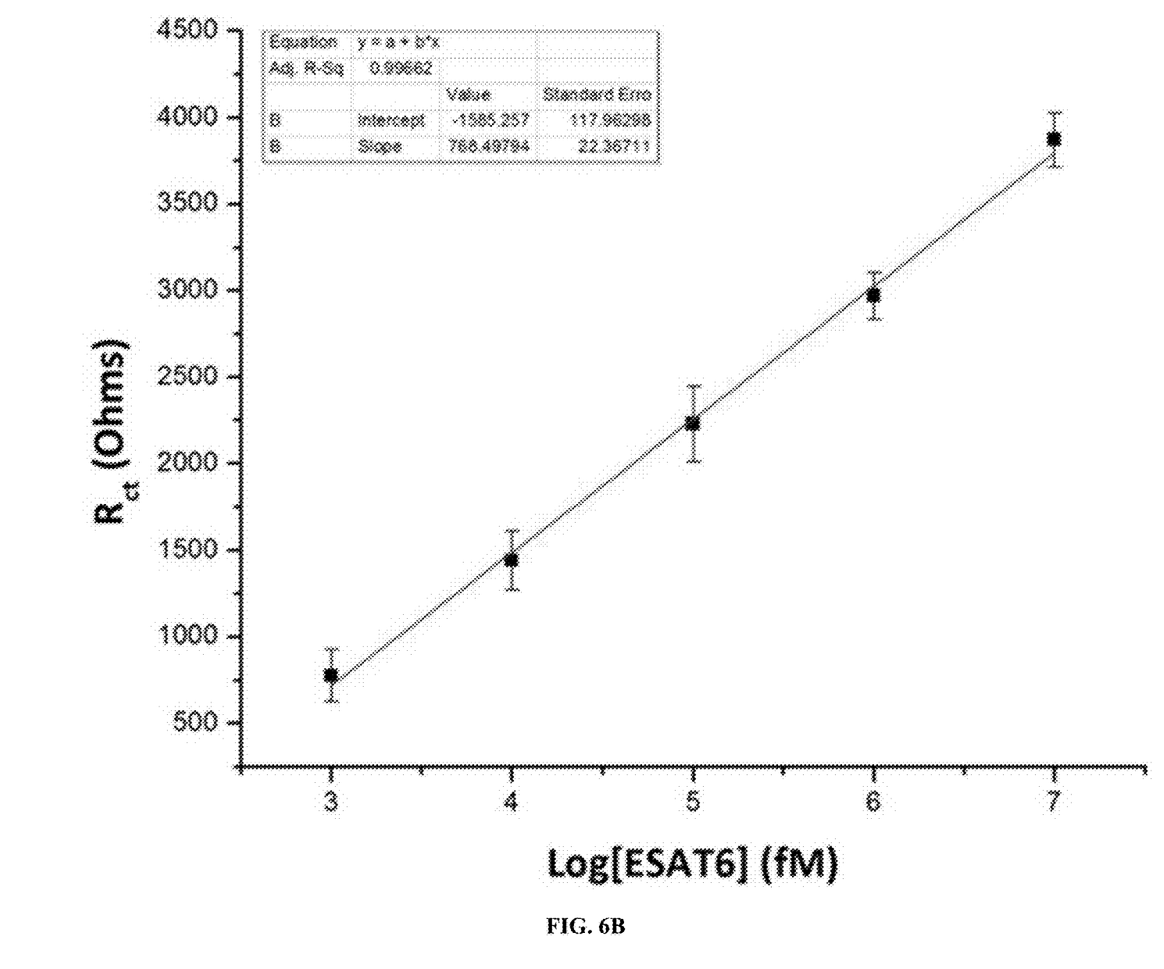

Then, based on electrochemistry, recombinant ESAT6 was detected using the selected EG11(44) aptamer. As a result, as illustrated in FIGS. 6A and 6B, it was confirmed from the Nyquist equation that, as the concentration of ESAT6 increased (1 pM to 10 nM), the impedance value increased (see FIG. 6A). The impedance value obtained from the Nyquist equation was set as a y-axis and the Log value of ESAT6 concentration was set as an x-axis to thereby obtain a graph, and it was confirmed that ESAT6 detection was quantitatively performed using the manufactured biosensor, and the detection limit was 1.15 fM (see FIG. 6B).

Example 8

Confirmation of Binding Specificity of Aptamer for ESAT6 Detection

In order for the DNA aptamer to be used as a biosensor, binding specificity thereof that does not react with various proteins in blood other than the target ESAT6 is important, and thus to confirm whether the DNA aptamer selectively binds to ESAT6, binding specificity thereof to various protein samples was examined. At this time, each protein was mixed at a concentration of 10 pM with PBS and used for detection.

Figure 7:
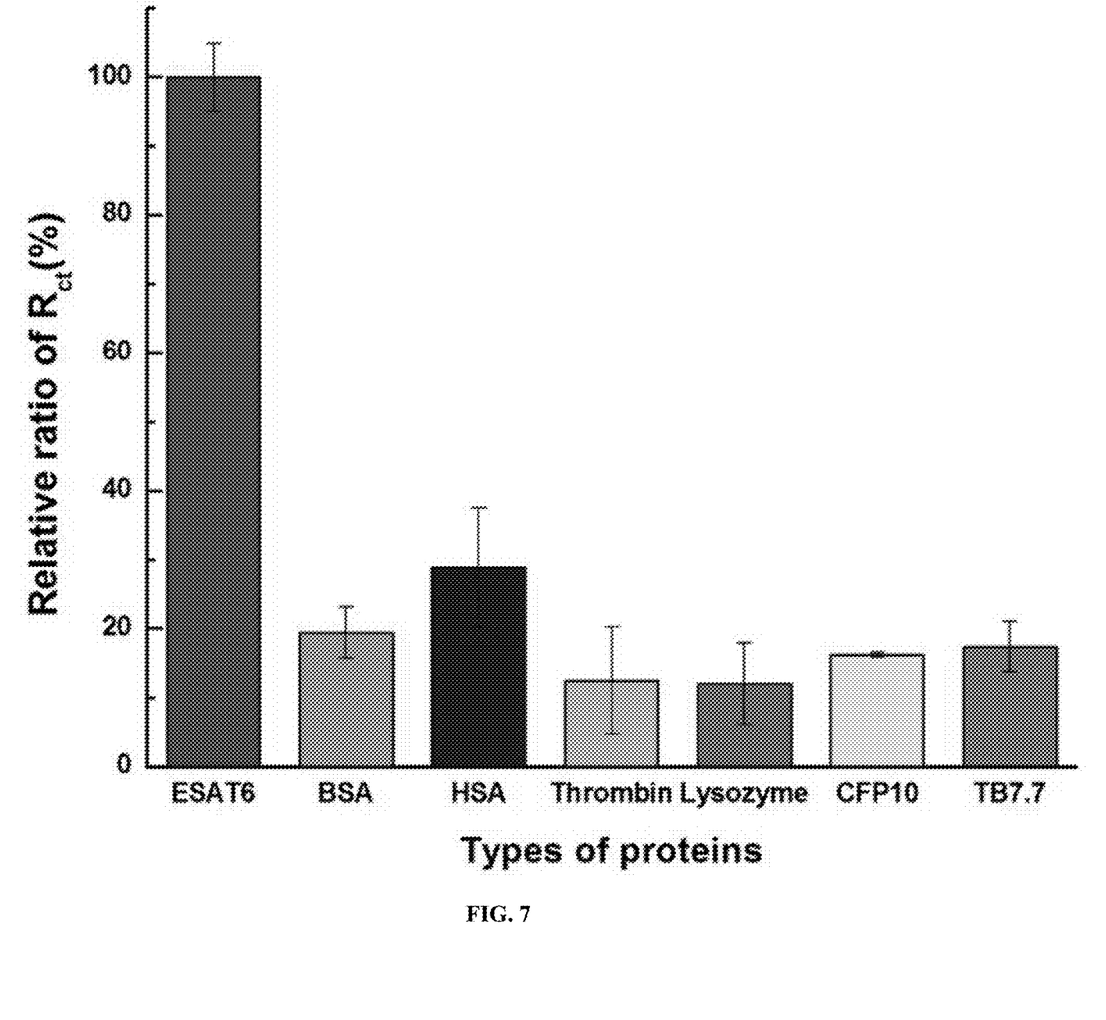
FIG. 7 illustrates results showing changes in relative impedance value according to reaction with each protein in a binding specificity experiment for the ESAT6 protein.

As a result, as illustrated in FIG. 7, it was confirmed that the DNA aptamer had excellent specificity for the ESAT6 protein. In particular, it was confirmed that, although ESAT6 is known to be overexpressed in a host with *Mycobacterium tuberculosis* and is a *Mycobacterium tuberculosis*-specific protein known to act by forming a complex with ESAT6, CFP-10 or TB7.7 did not bind to the DNA aptamer developed in the present invention. This means that the DNA aptamer of the present invention reacts with ESAT6 with high binding specificity.

Figure 8:
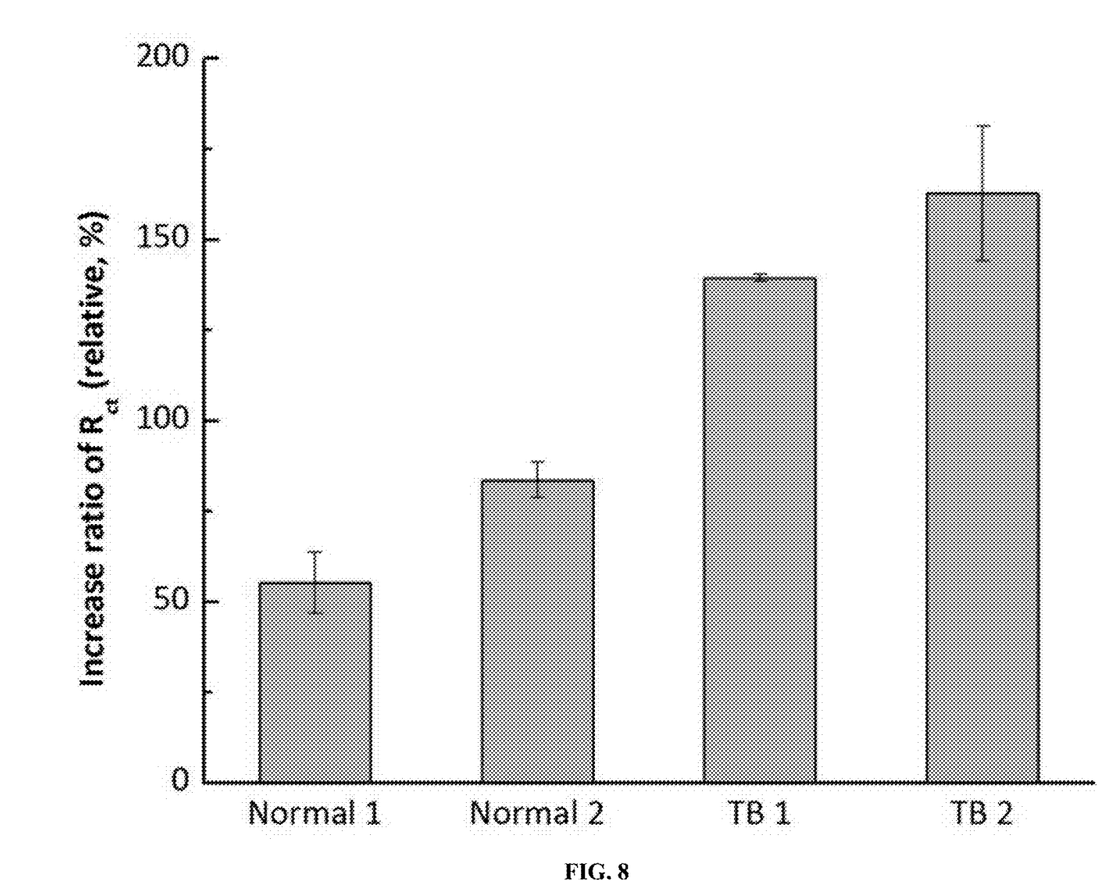
FIG. 8 illustrates results showing changes in impedance value when serum samples isolated from normal individuals and tuberculosis patients were treated with an EG11(44) aptamer.

Furthermore, to confirm whether this is applicable to clinical samples, 10 ng/ml of each of serum samples of normal individuals and tuberculosis patients was treated on an electrode on which the EG11(44) aptamer was immobilized, and as a result, as shown in FIG. 8, it was confirmed that a higher impedance value was shown in tuberculosis patients than in normal individuals.

From the above result, it means that the DNA aptamer EG11(44) developed in the present invention not only has very high binding specificity to ESAT6, but can also be used as a biosensor in complex biological samples.

For reference, the sequence list of the present invention is shown in Table 3 below.

TABLE 3

| Sequence list | Name | Sequence |
|---|---|---|
| SEQ ID NO: 1 | ESAT6 forward primer | cccggatcca tgacagagca gcagtggaat tt |
| SEQ ID NO: 2 | ESAT6 reverse primer | cccccaagct tctatgcgaa catcccagtg a |
| SEQ ID NO: 3 | ssDNA library | cacctaatac gactcactat agcggatccg anctggctcg aacaagcttg c |
| SEQ ID NO: 4 | Forward primer | cacctaatac gactcactat agcgga |
| SEQ ID NO: 5 | Reverse primer | gcaagcttgt tcgagccag |
| SEQ ID NO: 6 | EG11(44) aptamer | cgaggtagct tacccgctta tgttcactgt gggttgctgg ctcg |

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described embodiments should be construed as being provided for illustrative purposes only and not for purposes of limitation.

INDUSTRIAL APPLICABILITY

A DNA aptamer of the present invention targets ESAT6 expressed in Mycobacterium tuberculosis and exhibits high affinity for the target and low binding capacity for substances other than the target, and thus when used for diagnosing tuberculosis, false-negative responses and false-positive responses are excluded, thereby obtaining more accurate diagnosis results. Therefore, the DNA aptamer of the present invention, a composition for diagnosing tuberculosis using the same, a biosensor for diagnosing tuberculosis, a method of diagnosing tuberculosis, and the like can provide high reliability results in diagnosing tuberculosis, and thus are expected to be widely used to diagnose tuberculosis by replacing an ELISA method using existing antibodies and a method of diagnosing tuberculosis using existing aptamers.

What is claimed is:

1. A DNA aptamer that specifically binds to early secretory antigenic target 6 kDa (ESAT6), wherein the DNA aptamer consists of a nucleotide sequence of SEQ ID NO: 6.

2. The DNA aptamer of claim 1, wherein the ESAT6 is expressed in *Mycobacterium tuberculosis* H37Rv.

3. A composition for diagnosing tuberculosis, the composition comprising the DNA aptamer of claim 1.

4. A biosensor for diagnosing tuberculosis, the biosensor comprising: a DNA aptamer specific to early secretory antigenic target 6 kDa (ESAT6); and a board on which the DNA aptamer is immobilized, wherein the DNA aptamer consists of a nucleotide sequence of SEQ ID NO: 6.

5. The biosensor of claim 4, wherein the board consists of a metal electrode layer and a metal nanoparticle layer.

6. The biosensor of claim 5, wherein the metal comprises gold (Au).

7. A method of providing information for diagnosing tuberculosis, the method comprising:
(1) treating a subject sample to the biosensor of claim 4; and
(2) measuring a level of early secretory antigenic target 6 kDa (ESAT6) bound to the biosensor.

8. A method of diagnosing tuberculosis, the method comprising bringing the DNA aptamer of claim 1 into contact with a subject sample.

9. A method of diagnosing tuberculosis, the method comprising: treating a subject sample to the biosensor of claim 4; and measuring a level of early secretory antigenic target 6 kDa (ESAT6) bound to the biosensor.

* * * * *